(12) United States Patent
Lucas

(10) Patent No.: US 7,179,454 B2
(45) Date of Patent: Feb. 20, 2007

(54) PERSONAL CARE COMPOSITION FOR SHAVING

(75) Inventor: Sean A. Lucas, 2400 Hartfell Rd., Baltimore, MD (US) 31093

(73) Assignee: Sean A. Lucas, Baltimore, MD (US)

( * ) Notice: Subject to any disclaimer, the term of this patent is extended or adjusted under 35 U.S.C. 154(b) by 283 days.

(21) Appl. No.: 10/818,316

(22) Filed: Apr. 6, 2004

(65) Prior Publication Data

US 2005/0220748 A1 Oct. 6, 2005

(51) Int. Cl.
*A61Q 9/02* (2006.01)
*A61K 36/886* (2006.01)
*A61K 36/00* (2006.01)

(52) U.S. Cl. .......................... 424/73; 424/744; 424/725

(58) Field of Classification Search ................. 424/73, 424/744, 725
See application file for complete search history.

(56) References Cited

U.S. PATENT DOCUMENTS

| | | | |
|---|---|---|---|
| 4,551,330 A | 11/1985 | Wagman et al. | |
| 5,783,534 A | 7/1998 | Wahle et al. | |
| 5,914,103 A | 6/1999 | Armbruster et al. | |
| 5,958,394 A | 9/1999 | Smith | |
| 6,106,849 A | 8/2000 | Malkan et al. | |
| 6,494,920 B1 | 12/2002 | Weuthen et al. | |
| 6,497,889 B2 | 12/2002 | Takekoshi et al. | |
| 6,537,534 B1 | 3/2003 | Armbruster et al. | |
| 6,537,564 B1 | 3/2003 | Mabratu | |
| 6,544,534 B2 | 4/2003 | Malmgren et al. | |
| 6,641,803 B1 | 11/2003 | Kahre et al. | |
| 2002/0034489 A1 | 3/2002 | Wiegland et al. | |
| 2002/0035046 A1 | 3/2002 | Lukenbach et al. | |
| 2002/0044977 A1 | 4/2002 | Close | |
| 2003/0028978 A1* | 2/2003 | Schulze zur Wiesche et al. ........................................................ 8/405 |

FOREIGN PATENT DOCUMENTS

| | | |
|---|---|---|
| JP | 55-104205 | 8/1980 |
| JP | 7-187965 | 7/1995 |

* cited by examiner

*Primary Examiner*—Patricia Leith

(57) ABSTRACT

The personal care composition for shaving is a pre-shaving conditioner for the skin and hair. The composition is water-based and includes aloe vera gel, vitamins A and E, an esterquat, preferably dipalmitoylethyldimonium chloride, and a thickener. A fragrance may be added to the composition if desired. The composition is applied to the area of skin that is to be shaven while in the shower. The composition should remain on the skin for at least two minutes and is then washed off. Once the composition is wiped off the skin, the user may shave in their traditional manner using a shaving cream or gel.

5 Claims, No Drawings

PERSONAL CARE COMPOSITION FOR SHAVING

BACKGROUND OF THE INVENTION

1. Field of the Invention

The present invention relates to a composition for a personal care shaving product that is applied to the skin. More particularly, the composition contains aloe vera gel to protect the skin while preparing hair for shaving.

2. Description of the Related Art

A plethora of pre-shaving or post-shaving products are available for protecting the skin and preparing hair for shaving. Pre-shaving products try to prepare the hair by softening the hair and skin before shaving. Then a shaving cream is applied to the skin and the hair is cut. Once the hair is cut, a user may apply any number of post-shaving products to the skin to hydrate the skin, soothe the skin, and reduce skin irritation. A pre-shaving composition is needed that can soften hair and skin prior to shaving and leave the skin moisturized after shaving.

Several personal care products have been developed for shaving purposes. U.S. Pat. No. 6,494,920, issued to Weuthen et al. on Dec. 17, 2002, discloses a cleaning composition comprising an esterquat and aloe that is used in cleaning textiles, hair and skin. U.S. Pat. No. 5,914,103, issued to Armbruster et al. on Jun. 22, 1999, describes a shaving lotion for use prior to and after shaving with an electric razor. The lotion comprises mainly water and alcohol with varying amounts of camphor, dimethyl glucose, isopropyl palmate, isopropyl myristate, vitamin E linoleate, vitamin A palmatate, ascorbic acid, titanium dioxide, zinc oxide, aloe vera gel, fragrance, carbopol 940, triethanolamide, carrageenan, glycerin, methyl paraben, propyl paraben and allantoin.

U.S. Pat. No. 6,537,534, issued to Armbruster et al. on Mar. 25, 2003, describes a shaving gel cream used in a waterless shaving system. The gel is applied to dry skin to keep hair dry and erect as a blade cuts the hair. The gel is about 50–70% water and includes about 1–5% aloe vera gel, 0.05–0.5% vitamin A, and 0.1–5% vitamin E acetate.

U.S. Pat. No. 5,958,394, issued to Smith on Sep. 28, 1999, discloses a shaving preparation aid that lubricates the skin, conditions skin and extends the life of a razor blade. The shaving aid uses a mucilte or fiber such as fiber psyllium and may contain aloe vera, and vitamin E. The composition would have a water-alcohol weight ratio of about 16:1 to about 11:1.

U.S. Patent Publication Number 2002/0035046, published on Mar. 21, 2002, discloses a personal care composition suitable for people having sensitive skin and eyes. The formula has at least one ester and a water dispersible component. The formula composition comprises an optional liquid silicone, a water dispersible component, an ester, a polymeric emulsifier and/or thickener and a skin, hair or nail benefiting agent.

U.S. Patent Application Number 2002/0034489, published on Mar. 21, 2002, discloses a method for depositing benefit agents on a keratinous surface, such as skin, hair and nails. The method comprises applying to a surface a gel comprising the a surfactant phase, an oil phase and a benefit agent. The gel was prepared having components of salicyclic acid, oil soluble surfactants or emulsifiers and water soluble salts, such as humectants. The surfactant comprises at least one amphoteric surfactant, at least one nonionic surfactant and at least one anionic surfactant.

U.S. Pat. No. 4,551,330, issued to Wagman et al. on Nov. 5, 1985, discloses a skin and hair conditioner composition and method. The composition comprises an oil-in-water emulsion including water, water-insoluble, unctuous, oleaginous material, a water-dispersible emulsifying agent, metal salts, and acid or alkali.

U.S. Pat. No. 6,544,534, issued to Malmgren et al. on Apr. 8, 2003, discloses a skin conditioner having sea salt, Epson salt, almond oil, apricot kernel oil, avocado oil, jojoba oil, aloe vera gel, castor oil, vitamin E, vegetable glycerin and soap.

Other cosmetics are disclosed in Japanese Patent Number 55-104,205 published on Aug. 9, 1980; Japanese Patent Number 7-187,965 published on Jul. 5, 1995; U.S. Pat. No. 6,537,564, issued to Mabratu on Mar. 25, 2003 (hair relaxer and conditioner consisting of coffee, walnut oil, fish oil, carnauba, milk, and honey); U.S. Patent Publication Number 2002/0044977, published on Apr. 18, 2002 (plant extract useful in cosmetics, therapeutic and prophylactic applications); U.S. Pat. No. 6,106,849, issued to Malkan et al. on Aug. 22, 2000 (a personal care product using acemannan as the carrier for an active cleansing ingredient); and U.S. Pat. No. 6,497,889, issued to Takekoshi et al. on Dec. 24, 2002. Products developed for cleaning are disclosed in U.S. Pat. No. 6,402,976, issued to Wahle et al. on Jun. 11, 2002; and U.S. Pat. No. 6,641,803, issued to Kahre et al. on Nov. 4, 2003.

None of the above inventions and patents, taken either singly or in combination, is seen to describe the instant invention as claimed. Thus a personal care composition for shaving solving the aforementioned problems is desired.

SUMMARY OF THE INVENTION

The personal care composition for shaving of the present invention is a pre-shaving conditioner for the skin and hair. The composition is water-based and includes aloe vera gel, vitamins A and E, an esterquat, such as dipalmitoylethyldimonium chloride, and a thickener. The conditioning agent used in this composition is dipalmitoylethyldimonium chloride, but other cationic detergents, film formers and proteins could be substituted for this ingredient. A fragrance may be added to the composition if desired. The composition is applied to the area of skin that is to be shaven while in the shower. It should remain on the skin for at least two minutes and is then washed off. Once the composition is wiped off the skin, the user may shave in their traditional manner using a shaving cream or gel. The user will notice the area of the skin and hair to which the composition is applied will be soft and conditioned, reducing the likelihood of a razor jumping during shaving and causing a nick or cut on the skin. After the area on the skin is shaven, the skin will remain soft and conditioned, so that there is no need to apply a post-shaving product.

These and other features of the present invention will be readily apparent upon review of the following specification.

DETAILED DESCRIPTION OF THE PREFERRED EMBODIMENTS

The present invention relates to a personal care composition for softening skin and hair in preparation for shaving. The composition includes water, an ester quaternary, a thickener, and aloe vera gel. Optional additives, such as vitamins and fragrance, can be added to the composition.

The ester quaternary, or "esterquat", is a conditioning agent used in the personal care industry to condition and control static in hair care formulas. The esterquat is a quaternized fatty acid triethanolamine ester salt. Esterquats are known compounds that may be obtained using organic chemistry methods of partially esterifying triethanolamine with fatty acids, and then using organic solvents, such as dimethyl sulfate or ethylene oxide, to quaternize the reaction product. U.S. Pat. No. 6,494,920, issued on Dec. 17, 2002, and particularly the discussion of esterquats therein, is hereby incorporated by reference. A preferred esterquat used in the composition is dipalmitoylethyldimonium chloride. Dipalmitoylethyldimonium chloride is the conditioning agent used in this composition, but other cationic detergents, film formers and proteins could be substituted for this ingredient.

The thickener used in the composition is preferably cellulose. Aloe vera gel is also added to the composition. Aloe vera is a colorless mucilaginous gel obtained from the parenchymatous cells in the fresh leave of an aloe vera plant. The aloe vera plant is a succulent, being of the tree lily (Liliaceae) family. It is grown commercially in warm regions of the world. Aloe vera soothes the skin, reduces itching, and relieves skin irritation.

The composition also preferably comprises vitamins A and E and, optionally, a fragrance. The water used in the composition may be deionized water. The composition includes (1) about 40% by volume water; (2) about 32% to 52% by volume dipalmitoylethyldimonium chloride; (3) about 2% to 12% by volume cellulose; (4) 4% to 10% by volume aloe vera gel; (5) about 0.05% by volume vitamin A; (6) about 0.05% by volume vitamin E; and (7) about 1% by volume fragrance. In the preferred embodiment, the composition includes (1) 40% by volume water; (2) 32% by volume dipalmitoylethyldimonium chloride; (3) 22% by volume cellulose; (4) 4% by volume aloe vera gel; (5) 0.05% by volume vitamin A; (6) 0.05% by volume vitamin E; and (7) 1% by volume fragrance.

The composition is a cream that is applied to the area of the skin that is to be shaven. A user will rub in a dime size amount, or less, of the composition on wet skin. The composition is allowed to remain on the skin for between two to five minutes. Allowing the composition to diffuse through the skin and hair imparts better skin and hair conditioning results. The composition is then washed off and the user shaves in any traditional manner using a shaving cream or gel within or less than five minutes of washing off the composition.

The user of the personal care composition will notice the shaving process is made easier because the hair or stubble is softened, allowing it to be cut effortlessly by a razor. The user will also notice the ease in which the razor glides across the skin, reducing nicks and cuts associated with shaving. The shaven skin will be conditioned and soft, so that there is no need to apply an aftershave lotion or balm, as the skin is already hydrated and moisturized by the composition of the present invention.

As an added feature of using the composition the user will notice a longer life span for their razor. Most shavers replace their razor or blades every one to three weeks. The composition softens the hair or bristle to an extent that will slow down the rate of the razor dulling.

It is to be understood that the present invention is not limited to the embodiments described above, but encompasses any and all embodiments within the scope of the following claims.

I claim:

1. A personal care composition for shaving, consisting essentially of, by volume:
   about 40% water;
   between about 32% to 52% esterquat;
   between about 12% and 22% thickener;
   between about 4% and 10% aloe vera gel;
   about 0.5% vitamin A; and
   about 0.5% vitamin E.

2. The personal care composition according to claim 1, wherein said esterquat is dipalmitoylethyldimonium chloride.

3. The personal care composition according to claim 1, wherein said thickener is cellulose.

4. The personal care composition according to claim 1, further comprising about 1% by volume of a fragrance.

5. A method of using the personal care composition of claim 1 for shaving, comprising the steps of:
   applying the composition to an area of the skin to be shaved;
   leaving the composition on the skin for between about two minutes and five minutes so that the composition diffuses through the skin and hair;
   washing the composition from the skin; and
   shaving the area.

* * * * *